United States Patent [19]

Schinzel

[11] 4,309,536

[45] Jan. 5, 1982

[54] PROCESS FOR THE MANUFACTURE OF BIS-BENZO-FURANYL COMPOUNDS

[75] Inventor: Erich Schinzel, Hofheim, Fed. Rep. of Germany

[73] Assignee: Hoechst Aktiengesellschaft, Fed. Rep. of Germany

[21] Appl. No.: 186,400

[22] Filed: Sep. 11, 1980

[30] Foreign Application Priority Data

Sep. 14, 1979 [DE] Fed. Rep. of Germany ....... 2937231

[51] Int. Cl.$^3$ ................. C07D 407/06; C07D 407/10; C07D 407/14
[52] U.S. Cl. ................ 542/454; 260/346.22; 260/346.71; 260/346.73; 542/459; 542/466
[58] Field of Search ....... 542/454, 459, 466; 260/346.22, 346.71, 346.73

[56] References Cited

U.S. PATENT DOCUMENTS 3,859,350  1/1975  Sahm et al. ................ 542/454
3,932,301  1/1976  Crounse et al. ............. 542/459
3,974,172  8/1976  Sahm et al. ................ 542/459
4,122,257  10/1978  Prossel et al. ............. 542/454
4,133,953  1/1979  Schinzel ................... 542/454
4,230,624  10/1980  LeCorre et al. ............. 260/346.22

*Primary Examiner*—Arthur P. Demers
*Attorney, Agent, or Firm*—Connolly and Hutz

[57] ABSTRACT

Process for the manufacture of optically brightening bis-benzofuranyl compounds by cyclization of compounds of the formula

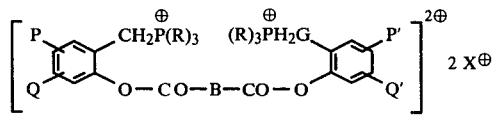

in aprotic solvents and in the presence of alkali metal or alkaline earth metal carbonates.

7 Claims, No Drawings

PROCESS FOR THE MANUFACTURE OF BIS-BENZO-FURANYL COMPOUNDS

It has been proposed to manufacture benzofurane compounds by cyclization of o-acyloxy-benzyl phosphonium salts. DOS No. 2,837,736, for example, describes a process of this type wherein bases from the group of the hydroxides and alcoholates of alkali metals, such as sodium t-amylate and potassium t-butylate or sodium hydroxide and potassium hydroxide, are used as cyclization agents. Attempts to manufacture bis-benzofurane derivatives under the conditions indicated in the specification failed. Strongly colored, non fluorescent reaction products that are mostly soluble in alkalis have been obtained.

It has now been found that bis[benzofuranyl-(2)] compounds of the formula I

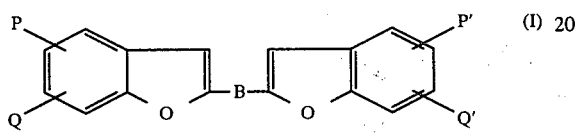

in which B denotes a direct link or one of the following groups

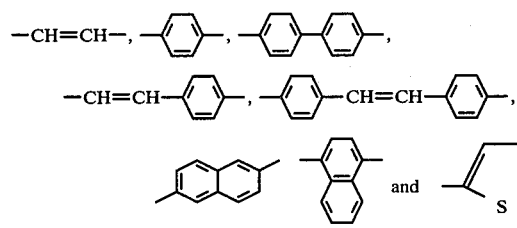

P; Q, P' and Q', independent of one another, are hydrogen or halogen atoms, lower alkoxy or phenyl, optionally functionally modified carboxy groups, or P and Q as well as P' and Q' together denote a fused benzene nucleus, can be produced by subjecting to cyclization compounds of the formula II

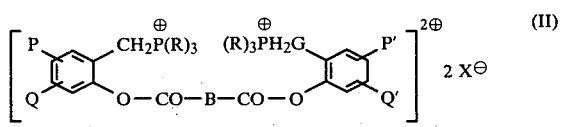

in which B, P, Q, P' and Q' are as defined above and
R denotes alkyl, aryl or aralkyl and
X stands for an anion,
in aprotic solvents and in the presence of alkali metal or alkaline earth metal carbonates.

Suitable carbonates are, preferably, sodium or potassium carbonate. It proved advantageous to use said condensation agents in dried, anhydrous form. 2 Mols of carbonate are used for each mol of compound II, an excess up to two times the molar amount has no detrimental effect.

Aprotic solvents to be used are anhydrous, aromatic hydrocarbons such as toluene, xylenes, xylene mixtures, chlorobenzene, o-dichlorobenzene, 1,2,4-trichlorobenzene, trichlorobenzene mixtures, α-methylnaphthalene, mixtures of α- and β-methylnaphthalene, α-chloronaphthalene and tetrahydronaphthalene. There are preferred chlorinated hydrocarbons such as chlorobenzene, o-dichlorobenzene and trichlorobenzene. Compounds II and the carbonates used as cyclization agents are very little soluble only in the aforesaid solvents and, therefore, the reaction substantially proceeds in a heterogeneous phase. In general, the reaction products I are also sparingly soluble in the solvents used and, therefore, they can be isolated simply by suction-filtration and washing and obtained in a pure form.

Depending on the character of connecting link B and of substituents P, Q, P' and Q' the most favorable reaction temperature is in the range of from 100° to 200° C., preferably 130° to 180° C. It proved advantageous to operate at the boiling point of the chosen solvent while using a water separator. Under such conditions the water formed from the carbonates is continuously removed so that it cannot cause splitting of the ester linkage in the starting compounds II. In order to support this process and to protect compounds I and II against oxidation, a weak current of dried nitrogen should be passed over the reaction mixture.

Compounds of the formula (II) are obtained in known manner by the following reaction by side chain halogenation of bis-o-cresyl esters (IV) to give bis-benzyl halides (III) which, on their part, are then reacted with phosphines P(R$_3$).

In the formulae B, P, Q, P', Q' and R are as defined above and X denotes halogen.

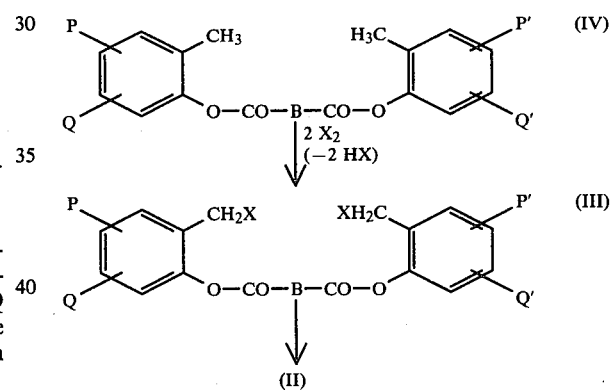

By selecting appropriate solvents and reaction conditions two or more stages of the above synthesis and the cyclization of the invention of compounds (II) can be combined to a "one vessel process". For example, bis-benzyl halides (III) can be reacted in o-dichlorobenzene with triphenyl phosphine to give the bis-phosphonium salts (II) which are then subjected to cyclization, without intermediate isolation, by addition of 2 mols of sodium carbonate to give the compounds (I).

The process of the invention provides a simple way to synthesize bis-[benzofuranyl-(2)] compounds which are valuable optical brighteners and starting products therefor to be used in several fields of application in textile and detergent industries.

The term functionally modified carboxy group indicated above for P, Q, P' and Q' is intended to include, in the first place, salts thereof with colorless cations, preferably alkali metal or ammonium ions, and also functional derivatives of a carboxy group in which three bonds of the carbon atom carry hetero atoms, preferably the cyano group, a carboxylic acid ester group or a carboxylic acid amide group. Suitable carboxylic acid ester groups are preferably those of the formula COOR[1] in which R[1] denotes phenyl or an optionally branched lower alkyl group, which groups R[1] may carry further substituents, for example an alkoxy group. Suitable carboxylic acid amide groups are preferably groups of the formula CONR[2]R[3] in which the radicals R[2] and R[3] denote hydrogen or lower alkyl or substituted alkyl groups which may form a hydroaromatic ring together with the nitrogen atom, and also acid hydrazides and the analogous thio-derivatives. The term "lower" is intended to mean groups having from 1 to 4 carbon atoms.

The following bis[benzofuranyl-(2)] compounds can be obtained, for example, by the process of the invention:

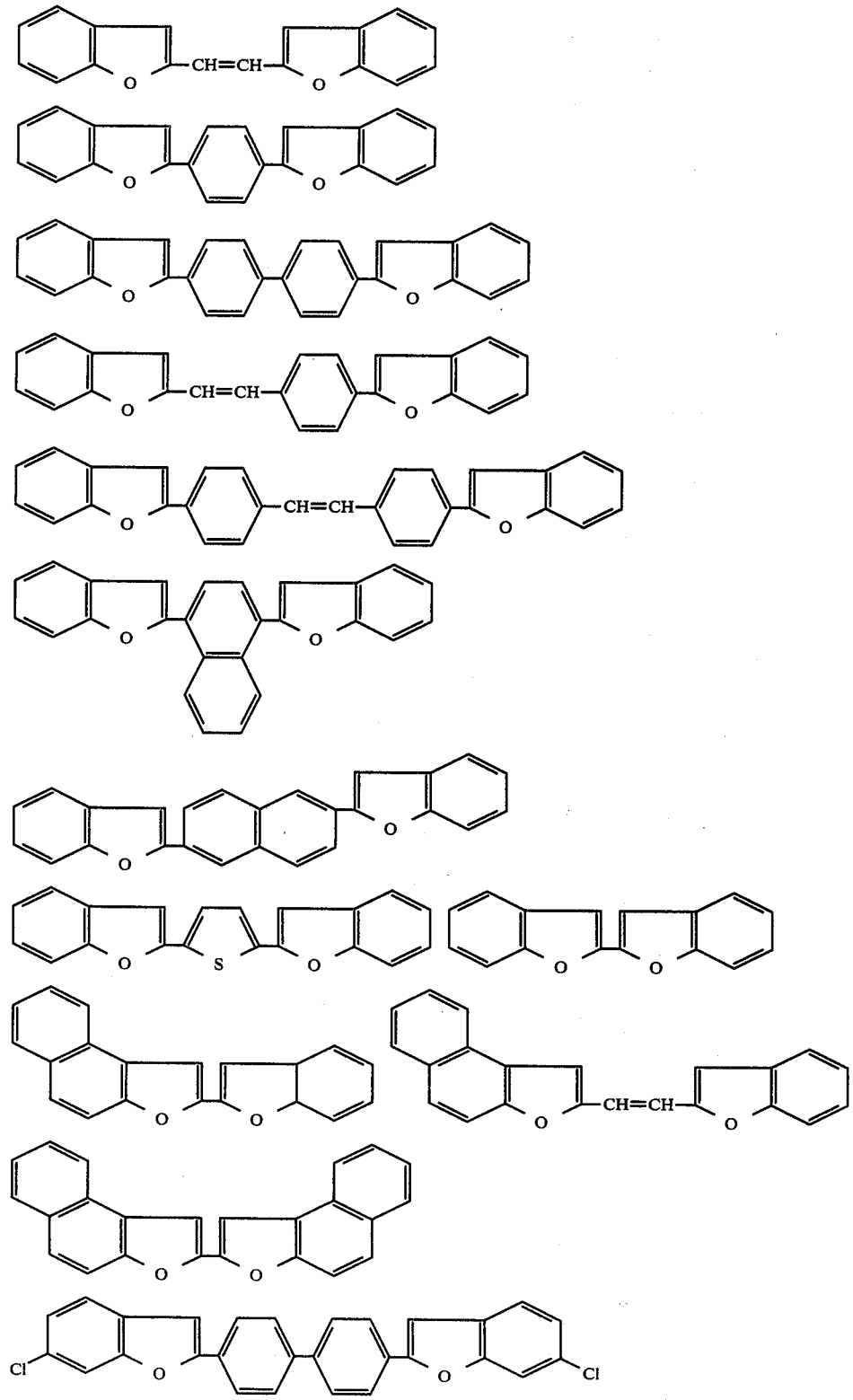

-continued

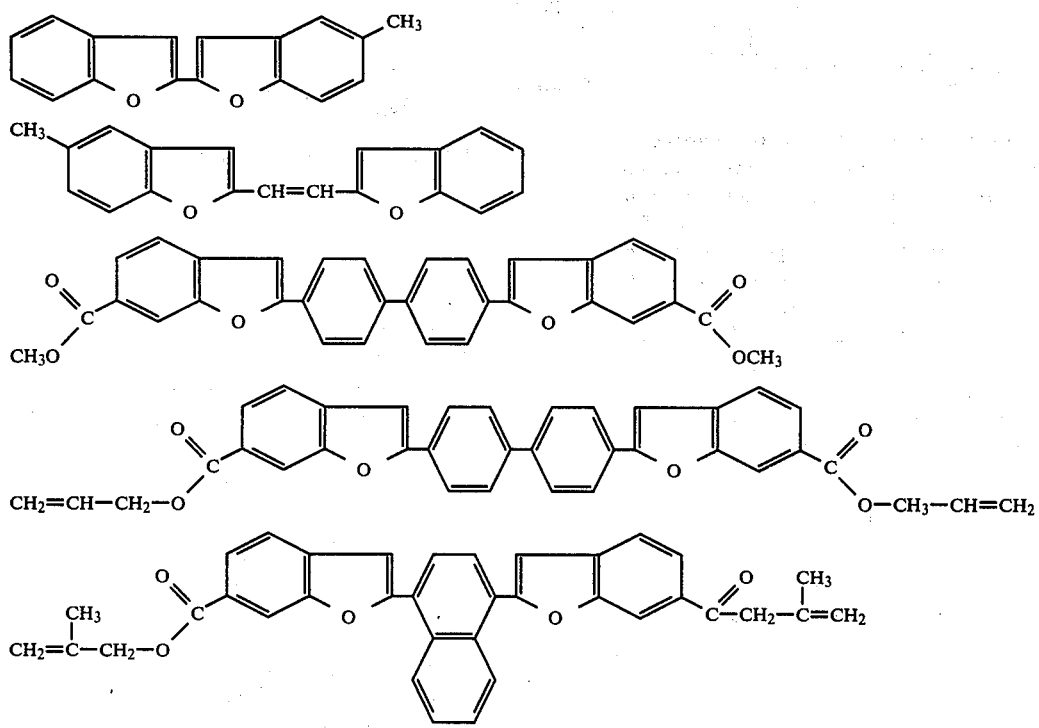

The following Examples illustrate the invention.

EXAMPLE 1

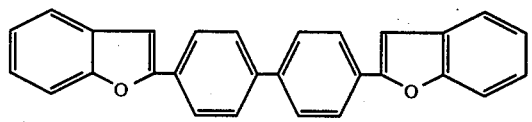 (1)

27.62 g of the bis-phosphonium salt (2) are added to 60 ml of o-dichlorobenzene, 8.6 g of potassium carbonate (dried and pulverized) are added and the mixture is heated to boil while thoroughly stirring and passing over a weak nitrogen current. The mixture is boiled for 4 hours on a water separator, cooled to room temperature and filtered off with suction. The residue on the suction filter is repeatedly covered with methanol and washed with water until neutral. After drying at 60° C. in vacuo, 7.34 g of 4,4'-bis[benzofuranyl-(2)]-biphenyl(1) melting at 350° to 360° C. are obtained as yellowish crystal powder, corresponding to a yield of 76% of the theoretical. The same yield of compound (1) is obtained with the use of anhydrous sodium carbonate.

The bis-phosphonium salt (2)

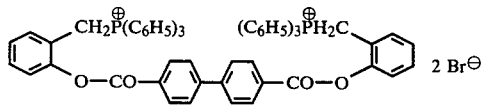 (2)

is prepared as follows:

58 g of the bis-bromomethyl compound (3) are added while stirring to 500 ml of o-dichlorobenzene and 57.7 g of triphenyl-phosphine are admixed. At 90° C. first a clear solution is formed from which the phosphonium salt separates after a short while. Stirring of the mixture is continued for 3 hours at 95° to 100° C., the mixture is allowed to cool to room temperature and filtered off with suction. The filter residue is repeatedly washed with o-dichlorobenzene and toluene and dried in vacuo at 60° C. 107.7 g of the bis-phosphonium compound (2) are obtained in the form of a colorless powder melting at 259° to 264° C., corresponding to a yield of 97.5% of the theoretical.

The bis-bromomethyl compound (3)

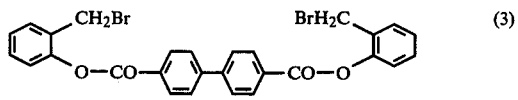 (3)

is prepared as follows:

148 g of diphenyl-dicarboxylic acid dicresyl ester (4) are dissolved in 1.5 l of carbon tetrachloride while stirring at boiling temperature. After cooling to 60° C., 124.6 g of N-bromosuccinimide and 1.4 g of azoisobutyric acid dinitrile are added and the mixture is again heated to boil. It is refluxed for 1 hour while radiating with ultraviolet light, cooled to 5° C. and filtered off with suction. The filter residue is washed twice with carbon tetrachloride and dried in vacuo at 60° C. The colorless powder obtained is digested at room temperature with 1.5 l of water, filtered off, washed with water and dried again. 157.9 g of crude compound (3) are obtained in the form of a light yellow powder melting at 182.5° to 191° C., corresponding to 78% of the theoretical. After recrystallization from toluene, the bis-bromomethyl compound (3) melts at 190.5° to 194° C.

To prepare the bis-o-cresyl ester of diphenyl-dicarboxylic acid (4)

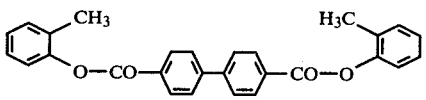

(4)

139.5 g of diphenyl dicarboxylic acid chloride are added at room temperature to 250 ml of o-dichlorobenzene and 105 ml of o-cresol are added thereto while stirring. The mixture is heated to boil during the course of 30 minutes and while passing over nitrogen and refluxed for 2 hours until no more hydrogen chloride can be detected. The reaction mixture is cooled, diluted with 350 ml of ethanol and stirring is continued for 1 hour at +5° C. The mixture is filtered off with suction, the filter residue is repeatedly washed with ethanol and dried at 60° C. in vacuo. 200.7 g of compound (4) melting at 152° to 154.5° C. are obtained, corresponding to a yield of 95% of the theoretical.

EXAMPLE 2

58 g of the bis-bromomethyl compound (3) are added at room temperature to 500 ml of o-dichlorobenzene and, while stirring, 57.7 g of triphenyl phosphine are added. The mixture is heated to 100° C., maintained at said temperature for 3 hours and then 21.2 g of sodium carbonate (dried and pulverized) are added. The reaction mixture is heated to boil while passing over a weak nitrogen current, boiled for 4 hours at a water separator, cooled and filtered off at room temperature. The filter residue is repeatedly covered with methanol and washed with water until neutral. After drying at 60° C. in vacuo, 29.6 g of 4,4' bis[benzofuranyl-(2)]-biphenyl (1) melting at 356° to 360° C. are obtained in the form of a light yellow powder, corresponding to a yield of 76.7% of the theoretical referred to starting compound (3).

What is claimed is:

1. Process for the manufacture of bis[benzofuranyl-(2)] compounds of the formula (I)

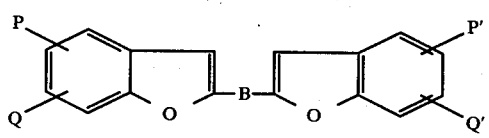

(I)

in which B denotes a direct link or one of the following groups

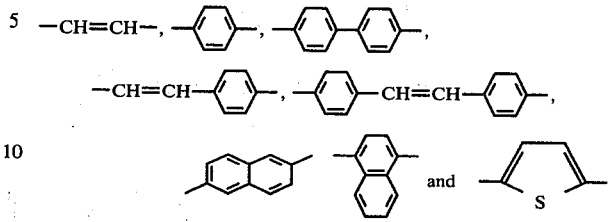

P, Q, P' and Q', independent of one another, are hydrogen or halogen atoms, lower alkoxy or phenyl, optionally functionally modified carboxy groups, or P and Q as well as P' and Q' together denote a fused benzene nucleus, which comprises subjecting compounds of the formula II

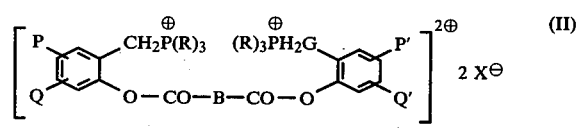

(II)

in which B, P, Q, P' and Q' are as defined above and
R denotes alkyl, aryl or aralkyl and
X stands for an anion,
in an aprotic solvent and in the presence of an alkali metal or alkaline earth metal carbonate to a cyclization reaction.

2. The process of claim 1, wherein sodium carbonate or potassium carbonate is used as cyclization agent.

3. The process of claim 1, wherein aromatic hydrocarbons substituted by alkyl groups or halogen atoms are used as aprotic solvent.

4. The process of claim 1, wherein chlorinated hydrocarbons such as chlorobenzene, o-dichlorobenzene or trichlorobenzene are used as aprotic solvent.

5. The process of claim 1, wherein the cyclization is carried out at temperatures of from 100° to 200° C., preferably 130° to 180° C.

6. The process of claim 1, wherein the cyclization is carried out while simultaneously distilling off the water formed from the carbonate.

7. The process of claim 1, wherein the cyclization is carried out while passing over a weak nitrogen current.

* * * * *